US006759126B1

(12) United States Patent
Malik et al.

(10) Patent No.: US 6,759,126 B1
(45) Date of Patent: Jul. 6, 2004

(54) SOLID PHASE MICROEXTRACTION FIBER STRUCTURE AND METHOD OF MAKING

(75) Inventors: Abdul Malik, Lutz, FL (US); Dongxin Wang, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 09/806,443

(22) PCT Filed: Aug. 20, 1999

(86) PCT No.: PCT/US99/19013

§ 371 (c)(1),
(2), (4) Date: Jul. 13, 2001

(87) PCT Pub. No.: WO00/17429

PCT Pub. Date: Mar. 30, 2000

Related U.S. Application Data
(60) Provisional application No. 60/102,481, filed on Sep. 30, 1998, and provisional application No. 60/101,232, filed on Sep. 21, 1998.

(51) Int. Cl.[7] ............................. D02G 3/00; B32B 9/00
(52) U.S. Cl. ...................... 428/391; 428/375; 428/392; 428/398
(58) Field of Search ................................ 428/375, 378, 428/391, 392, 398

(56) References Cited

U.S. PATENT DOCUMENTS

| | | | | |
|---|---|---|---|---|
| 4,636,440 A | * | 1/1987 | Jada ........................... | 428/446 |
| 4,935,296 A | * | 6/1990 | Stevens ...................... | 428/288 |
| 5,124,374 A | * | 6/1992 | Baker et al. ................ | 428/931 |
| 5,130,194 A | * | 7/1992 | Baker et al. ................ | 438/367 |
| 5,209,976 A | * | 5/1993 | Ogawa ........................ | 428/391 |
| 5,378,521 A | * | 1/1995 | Ogawa et al. ................ | 428/85 |
| 5,445,886 A | * | 8/1995 | Ogawa ........................ | 428/403 |
| 5,571,622 A | * | 11/1996 | Ogawa et al. .............. | 428/391 |
| 5,629,088 A | * | 5/1997 | Ogawa et al. .............. | 428/391 |
| 5,691,206 A | | 11/1997 | Pawliszyn | |
| 5,716,704 A | * | 2/1998 | Ogawa et al. .............. | 428/391 |
| 5,720,798 A | | 2/1998 | Nickerson et al. | |
| 5,736,245 A | * | 4/1998 | Grabbe et al. .............. | 428/391 |
| 5,965,271 A | * | 10/1999 | Grabbe et al. .............. | 428/446 |
| 5,999,681 A | * | 12/1999 | Grabbe et al. .............. | 385/128 |
| 6,136,187 A | * | 10/2000 | Zare et al. ................ | 210/198.2 |

FOREIGN PATENT DOCUMENTS

| | | | |
|---|---|---|---|
| WO | WO 00/17429 | * | 3/2000 |

OTHER PUBLICATIONS

Hayes, J.D.; Malik, A. *J. Chromatogr. B*. 1997, in press. Sol–Gel Chemistry–based Ucon–coated Columns.
Wang, D.; Chong, S.L.; Malik, A., *Anal. Chem.* Sol–Gel Column Technology.
Arkles et al., in Silicon Compounds, Register and Review, Huls, 65–73, 1991.
Arthur et al., Anal. Chem., 64: 1960–66, 1992.
Arthur et al., J. Environ. Sci. Technol. 26: 979–83, 1992.
Arthur et al., Anal. Chem, 62: 2145, 1990.
Arthur et al., LC.GC. 10.; 656–61, 1992.
Berlardi et al., Water Pollut. Res. J. Can., 24: 179–91, 1989.
Blomberg, L.G., J. Microcol., 2:62–8, 1990.

(List continued on next page.)

*Primary Examiner*—Cynthia H. Kelly
*Assistant Examiner*—J. M. Gray
(74) *Attorney, Agent, or Firm*—Anton J. Hopen; Smith & Hopen, P.A.

(57) ABSTRACT

A solid phase microextraction (SPME) fiber including a fiber and a deactivated surface-bonded sol-gel coating on a portion of the fiber to form a solid phase microextraction coating on the portion of the fiber, wherein the solid-phase microextraction coating is capable of preconcentrating trace organic compounds in various matrices. A sol-gel method of preparing SPME fibers with chemically bonded stationary phase coatings that serve as solvent-free extraction media including the step of chemically bonding the sol-gel stationary phase with the SPME fiber surface during its creation through sol-gel reactions.

11 Claims, 8 Drawing Sheets

OTHER PUBLICATIONS

Brinker et al., Sol–gel Science, The Physics and Chemistry of Sol–gel Processing, Academic Press, San Diego, USA, 1990, Contents and Preface.
Buchholz et al., J. Anal. Chem., 66: 160–167, 1994.
Chong et al., Anal. Chem., 69: 3889–3898, 1997.
Coulibaly et al., Food Rev. Int. 12: 131–151, 1996.
Dislich, H., in Sol–gel Technology for Thin Films, Fibers, Preforms, Electronics, and Specialty Shapes, (L.C. Klein ed., Noyes Publications, Park Ridge, NJ, USA, 50–79, 1988).
Engelhardt et al., J. Chromatogr. 716: 27–33, 1995.
Fabes et al., J. Am Ceram. Soc. 73(4): 978–88, 1990.
Guo et al., Anal. Chem., 67: 2511–16, 1995.
Guo et al., J. Chromatographia, 43: 477–483, 1996.
Guo et al., J. Chromatogr., 744: 17–29, 1996.
Guo et al., J. Microcolumn Sep., 7: 485–491, 1995.
Hawthorne, S.B., Anal. Chem., 62: 633A–642A, 1990.
Hayes et al., HPCE'97 –Final Program 80–81, (Jan. 26–30, 1997, Anaheim, CA, USA).
Hirata et al., J. Microolumn Sep., 6: 443–437, 1994, Abstract.
Iwamoto et al., J. Sol–gel Sci. Technol., 4: 141–150; 1995.
Jinno et al., J. Chromatogr., 754: 137–144, 1996.
Klein, L.C., Sol–gel Technology for Thin Films, Fibers, Preforms, Electronics, and Specialty Shapes; Noyes Publication; Park Ridge, N.J., USA, 1988, Contents.
Liu et al., Anal. Chem., 69: 190–95, 1997.
Livage, J., in Applications of Organometallic Chemistry in the Preparation and Processing of Advanced Materials, (J.F. Harrod and R.M. Laine Eds., Kluwer Academic Publishing, The Netherlands, 1995), 3–25.
Livage et al., J. Solid St. Chem. 18: 259–341, 1988.
Lopez et al., J.AOAC Int. 76:, 864–880, 1993, Abstract.
Louch et al., J. Anal. Chem, 64: 1187–1199, 1992.
Mackenzie, J. D., Hybrid Organic–Inorganic Composites (ACS Symposium Series 585, American Chemical Society, Washington, D.C., 1995), 227–236, Abstract.
Majors, R.C., LC*GC. Int., 10: 93–101, 1997.
Minnich et al., J. AOAC Int., 1198–1204, 1996.
Mukherjee, S., "Supercritical drying in structural and microstructural evolution of gels: A critical review," in Ultrastructure Processing of Advanced Ceramics (Mackenzie J.D. and Ulrich D.R. eds., Wiley, New York, 1988), 747–759.
Poole et al., Anal. Chim. Acta. 236:, 3–42, 1990.
Potter et al., J. Chromatogr. 625: 247–55, 1992.
Prakash et al., Nature, 374: 439–443, 1995.
Ramsey, J.D.F., "Sol–gel Processing," in Controlled Particle, Droplet and Bubble Formation, (D.J. Wedlock ed., Butterworth, U.K., 1994), 1–37.
Reighard et al., Crit. Rev. Anal. Chem. 26: 61–99, 1996, Abstract.
Richter et al., Anal. Chem., 1033–1039, 1996.
Rotzsche, H., Stationary Phases in Gas Chromatography; Elsevier Scientific Publishing Company: Amsterdam, The Netherlands, 1991, Library catalogue reference page.
Sanchez et al., New J. Chem. 18: 1007–1047, 1994.
Scherer, G.W., "Aging and drying of gels," J. Non–Cryst. Solids, 100: 72–92, 1988.
Stark et al., J. Phys. Chem., 72: 2750–2754, 1968.
Supelco Corp., Bellefonte, P.A. Manufacturer data sheet, 1996.
Van der Vlis et al., J. Chromatogr. A., 333–341, 1994, Abstract.

Wang et al., (manuscript in preparation), Abstract.
Wang et al., Proc. 18$^{th}$ Intl. Symp. Cap. Chromatogr. (May 20–24, 1996, Riva del Garda, Italy), P. Sandra & G. Devos (eds.), Huthig Publishers: Germany, 505–513, 1996.
Westwood, S.A., (Ed.), Supercritical Fluid Extraction and Its Use in Chromatographic Sample Preparation, CRC Press, Boca Raton, Fl, USA, 1993, Library catalogue reference page.
Wilkes et al., Polymer Prep. 26: 300, 1985, Abstract.
Woolley et al., J. High Resolut. Chromatogr. & Chromatogr. Commun. 7: 329–332, 1984.
Zhang et al., J. Anal. Chem. 66: 844A–53A, 1994.
Zlotorzynski, A., Crit. Rev. Anal. Chem., 25: 43–76, 1995.
Mackenzie, J.D., "Hybrid Organic–Inorganic Materials: Sol–Gel Approach," ACS Symposium Series 585, 226–236, 1995.
Potter et al., "Detection of substituted benzenes in water at the pg/ml level using solid–phase microextraction and gas chromatography–ion trap mass spectrometry," Journal of Chromatography, 625:247–255, 1992.
Hirata et al., "Solvent–free Sample Introduction for Supercritical Fluid Chromatography Using Polymer Coated Fibers," J. Microcol. Sep., 6:443–447, 1994.
Lopex–Avila et al., "Evaluation of Soxtec Extraction Procedure for Extracting Organic Compounds from Soils and Sediments," Journal of AOAC International, 76: 864–880, 1993.
Westwood, S.A., "Supercritical Fluid Extraction and its Use in Chromatographic Sample Preparation," First Edition CRC Press, 1993.
Rotzsche, H., "Stationary Phases in Gas Chromatography," Journal of Chromatography Library, 48, Elsevier Science Publishers B. V., 1991.
Klein, L., "Sol–Gel Technology for thin Films, Fibers, Preforms, Electronics, and Specialty Shapes," Materials Science and Process Technology Series, Noyes Publications, 1988.
Brinker et al., "Sol–gel Science, The Physics and Chemistry of Sol–gel Processing," Academic Press, San Diego, USA, 97–233, 1990.
Van der Vlis et al., "Combined liquid–liquid electroextraction and isotachophoresis as a fast on –line focusing step in capillary electrophoresis," Journal of Chromatography A, 687:333–341, 1994.
Wilkes et al., "Ceramers": Hybrid Materials Incorporating Polymeric/Oligomeric Species into Inorganic Glasses Utilizing a Sol–Gel Approach, Polymer Preprints, 26(2): 300–302, 1985.
Reighard et al., Bridging the Gap Between Supercritical Fluid Extraction and Liquid Extraction Techniques: Alternative Approaches to the Extraction of Solid and Liquid Environmental Matrices, Critical Reviews in Analytical Chemistry, 26: 61–99, 1996.

* cited by examiner

SOLID PHASE MICROEXTRACTION FIBER STRUCTURE AND METHOD OF MAKING

CROSS REFERENCE TO RELATED APPLICATIONS

This patent application is a National Phase of PCT/US99/19013, filed Aug. 20, 1999, concerning a filing under 35 U.S.C. 371, claiming the benefit of priority under 35 U.S.C. §119(e) of U.S. Provisional Application Serial No. 60/102,481, filed Sep. 30, 1998, now abandoned, and U.S. Provisional application Ser. No. 60/101,232, filed Sep. 21, 1998, abandoned, which is incorporated herein by reference.

TECHNICAL FIELD

The present invention relates to solid phase microextraction fiber structure, e.g., for preconcentrating trace organic materials from various matrices, and to a method of making such a solid phase microextraction fiber.

INTRODUCTION

With ever increasing environmental and health concerns, the analytical capability for extraction and preconcentration of trace organic contaminants from aqueous, gaseous, and solid samples have become extremely important. Various forms of Soxhlet extraction,[1] liquid-liquid extraction,[2] accelerated solvent extraction,[3] microwave-assisted solvent extraction,[4] solid-phase extraction,[5] supercritical fluid extraction,[6,7] purge and trap,[8] and other methods[9-11] are traditionally used for this purpose. Some of these methods often employ large volumes of hazardous organic solvents, others are time-consuming, and/or expensive. Most of these methods require collection of the samples and their transportation to the laboratory for further processing. Incorrect sample handling during collection, transportation, and preservation may result in significant variability in analysis results. Solid-phase microextraction (SPME) technique, developed in 1989,[12] effectively overcomes these difficulties by eliminating the use of organic solvent and by allowing sample extraction and preconcentration to be done in a single step. The technology is more rapid and simple than the conventional methods. It is also inexpensive, portable, and sensitive.

In SPME, the outer surface of a solid fused silica fiber (approximately 1 cm at one end) is coated with a selective stationary phase. Thermally stable polymeric materials that allow fast solute diffusion, are commonly used as stationary phases. The extraction operation is carried out by dipping the coated fiber end into the sample matrix, and allowing time for the partition equilibrium to be established. The amount of an analyte extracted by the coating is described by Nernst's partition law.[13] The sensitivity of the method, is mostly governed by the partition coefficient of an analyte between the coating and the matrix.[14] Extraction selectivity can be achieved by using appropriate types of stationary phases that exhibit high affinity toward the target analytes. For liquid samples, stirring and salting out procedures are commonly used to aid the extraction process.[15,16]

SPME is normally followed by gas chromatography (GC) analysis, in which the extracted analytes are thermally desorbed in the GC injection port for introduction into a GC column. Currently SPME has also been interfaced with other separation techniques, including high performance liquid chromatography (HPLC),[17] and supercritical fluid chromatography (SFC).[18] A specially designed syringe is commonly used to facilitate safe fiber handling during sample extraction and subsequent thermal desorption of the extracted sample in the injection port of a gas chromatograph.

Solid-phase microextraction is predominantly performed on SPME fibers coated with nonpolar poly (dimethylsiloxane) (PDMS) stationary phases.[19-21] A significant drawback of such fibers is that their recommended operating temperatures are relatively low, and generally remain within the range of 200–270° C.[22] This is about 80–150° C. lower than the upper temperature limit for the same stationary phases when used in a GC column. Two factors are believed to be responsible for this. First, the stationary phase coating thickness on an SPME fiber is a few orders of magnitude higher than the stationary phase film thickness in a GC column. Stabilization of such a thick film is much more difficult than that of submicrometer thick films used in GC columns. Second, the lack of proper chemical bonding of the stationary phase coating with the fiber surface may also be responsible for the lower thermal stability of conventionally coated PDMS fibers.

The problem should be more difficult for SPME fibers with conventionally coated polar stationary phases, since immobilization of physically coated polar films (even of submicrometer thickness) is much more difficult than that for nonpolar films.[23,24] Achieving immobilization of thick polar coatings, as used in SPME, should be even more difficult. It is evident that future advancements in SPME technology should greatly depend on new scientific breakthroughs leading to the development of more efficient technologies for creating selective stationary phase coatings, and their chemical immobilization as thick films of enhanced operational stabilities (temperature, solvent, etc.).

SUMMARY OF THE PRESENT INVENTION

The present invention provides a new and useful solid phase microextraction fiber structure and a new and useful method of making such a fiber structure. The present invention uses sol-gel chemistry to provide a simple and convenient pathway for the synthesis of advanced material systems and applying them as surface coatings.[25,26] The sol-gel chemistry provides efficient incorporation of organic components into the inorganic polymeric structures in solution under extraordinarily mild thermal conditions.[27]

Among the advantages of the use of sol-gel technology in connection with the present invention are: (a) low costs, (b) unique ability to achieve molecular level uniformity in the synthesis of organic-inorganic composites, and (c) strong adhesion of the coating to the substrate due to chemical bonding.[28] The last of the above advantages is especially important for SPME.

A solid phase microextration fiber according to the present invention basically comprises a fiber, and a deactivated surface-bonded sol-gel coating on a portion of the fiber to form a solid phase microextraction coating on that portion of the fiber. The solid phase microextraction coating is capable of preconcentrating trace organic compounds in various matrices. The solid phase microextraction coating has the formula:

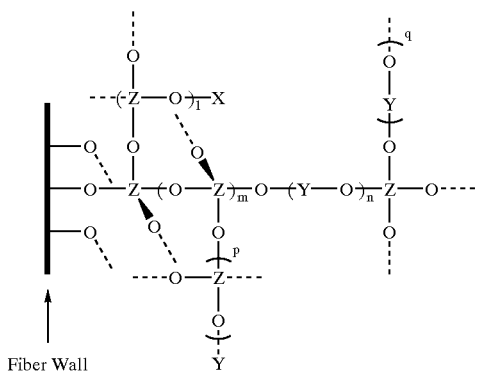

wherein,

X=Residual of a deactivation reagent;

Y=Sol-gel reaction residual of a sol-gel active organic molecules;

Z Sol-gel precursor-forming element l=an integer $\geq 0$;

m=an integer $\geq 0$;

n=an integer $\geq 0$;

p=on integer $\geq 0$;

q=an integer $\geq 0$; and (l, m, n, p and q are not simultaneously zero).

Dotted lines indicate the continuation of the chemical structure with X, Y, Z, or Hydrogen (H) in space.

The preparation of the solid phase microextraction fiber includes the steps of providing the fiber structure, providing a sol-gel solution comprising a sol-gel precursor, an organic material with at least one sol-gel active functional group, a sol-gel catalyst, a deactivation reagent, and a solvent system. The sol-gel solution is then reacted with a portion of the fiber (eg the tip of the fiber) under controlled conditions to produce a surface bonded sol-gel coating on the portion of the fiber. The fiber is then removed from the sol gel solution and is heated under controlled conditions to cause the deactivation reagent to react with the surface bonded sol-gel coating to deactivate and to condition the sol-gel coated portion of the fiber structure. Preferably, the sol-gel precursor includes an alkoxy compound. The organic material includes a monomeric or polymeric material with at least one sol-gel active functional group. The sol-gel catalyst is taken from the group consisting of an acid, a base and a fluoride compound, and the deactivation reagent includes a material reactive to polar functional groups (e.g., hydroxyl groups) bonded to the sol-gel precursor-forming element in the coating or to the fiber structure.

Additionally, the solid phase microextraction fibers made according to the present invention can be effectively used in combination with gas chromatography capillary columns and capillary electrochromatography columns described in concurrently filed U.S. Application Serial No. 60/102,483 entitled Capillary Column and Method of Making, incorporated herein by reference.

BRIEF DESCRIPTION OF DRAWINGS

Other advantages of the present invention will be readily appreciated as the same becomes better understood by reference to the following detailed description when considered in connection with the accompanying drawings wherein.

DETAILED DESCRIPTION OF THE INVENTION

As described above, the present invention relates to solid phase microextraction fibers for use as preconcentrators with trace organic compounds in various matrices. The following detailed description relates to solid phase microextraction fibers designed for use as preconcentrators with trace organic compounds in both polar and non polar analytes.

Figure 13A:
FIG. 13A is a schematic illustration of a solid phase microextration fiber made according to the principles of the present invention.
Figure 13B:
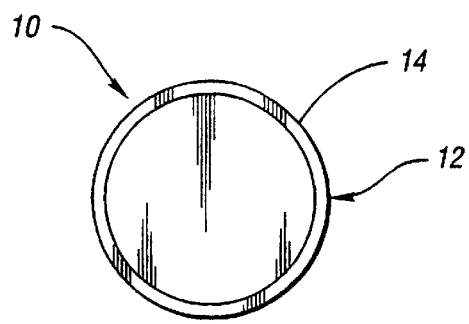
FIG. 13B is a side illustration of the fiber in FIG. 13.

FIGS. 13A and 13B show a solid phase microextraction fiber 10 made according to the principles of the present invention. The fiber includes a base fiber 12 and a coating 14 disposed on a portion (e.g. the tip portion) of the fiber. The fiber is coated in the manner described below, and is thereafter used as a preconcentrator, in the manner also described below.

A solid phase microextration fiber according to the present invention basically comprises a fiber, and a deactivated surface-bonded sol-gel coating on a portion of the fiber to form a solid phase microextraction coating on that portion of the fiber. The solid phase microextraction coating is capable of preconcentrating trace organic compounds in various matrices. The solid phase microextraction coating has the formula:

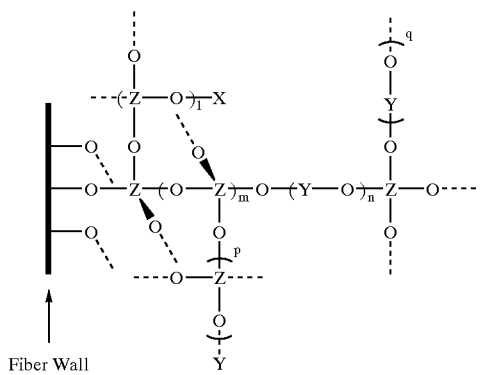

Fiber Wall wherein,
- X=Residual of a deactivation reagent (e.g., polymethylhydrosiloxane (PMHS), hexamethyldisilazane (HMDS) etc.);
- Y=Sol-gel reaction residual of a sol-gel active organic molecules (e.g., molecules with hydroxysilane or alkoxysilane functional groups or a combination thereof) either polymers or monomers, such as, polydimethylsiloxane (PDMS), polymethylphenylsiloxane (PMPS), polydimethyldiphenylsiloxane (PDMDPS), polyethylene glycol (PEG) and related polymers like Carbowax 20M, polyalkylene glycol such as Ucon, macrocyclic molecules like cyclodextrins, crown ethers, calixarenes, slkyl moieties like octadecyl, octyl, etc.;
- Z=Sol-gel precursor-forming element (e.g., Si, Al, Ti, Zr, etc.);
- l=an integer $\geq 0$;
- m=an integer $\geq 0$;
- n=an integer $\geq 0$;
- p=an integer $\geq 0$;
- q=an integer $\geq 0$; and (l, m, n, p, and q are not simultaneously zero).

Dotted lines indicate the continuation of the chemical structure with X, Y, Z, or Hydrogen (H) in space.

The preparation of the solid phase microextraction fiber includes the steps of providing the fiber structure, providing a sol-gel solution comprising a sol-gel precursor, an organic material with at least one sol-gel active functional group, a sol-gel catalyst, a deactivation reagent and a solvent system. The sol-gel solution is then reacted with a portion of the fiber (eg the tip of the fiber) under controlled conditions to produce a surface bonded sol-gel coating on the portion of the fiber. The fiber is then removed from the sol gel solution and is heated under controlled conditions to cause the deactivation reagent to react with the surface bonded sol-gel coating to deactivate and to condition the sol-gel coated portion of the fiber structure. Preferably, the sol-gel precursor includes an alkoxy compound. The organic material includes a monomeric or polymeric material with at least one sol-gel active functional group. The sol-gel catalyst is taken from the group consisting of an acid, a base and a fluoride compound, and the deactivation reagent includes a material reactive to polar functional groups (e.g., hydroxyl groups) bonded to the sol-gel precursor-forming element in the coating or to the fiber structure.

Equipment. SPME-GC experiments were carried out on a Shimadzu Model 14A capillary GC system equipped with an FID and a split-splitless injector. A Fisher Model G-560 Vortex Genie 2 system was used for thorough mixing of various ingredients in the sol solution. A Microcentaur Model APO 5760 centrifuge was used to separate the sol solution from the precipitate (if any). A homemade SPME syringe (FIG. 1) was used for the transfer of the extracted sample into the GC injector for analysis. It was assembled using spare parts purchased from Valco Instruments Co. Inc. (Houston, Tex., USA). A Barnstead Model 04741 Nanopure deionized water system was used to obtain 17.8MΩ water. On-line data collection and processing were done using ChromPerfect (Version 6.07) computer software (Justice Innovations, Mountain Views, Calif., USA). The scanning electron microscopy (SEM) experiments on the sol-gel PDMS fiber coatings were carried out on a JEOL JSM35 electron microscope.

Chemicals and materials. Fused silica fiber (220 μm o.d.), with protective polyimide coating, was obtained from Polymicro Technologies Inc. (Phoenix, Ariz., USA). Hydroxy-terminated poly(dimethylsiloxane) (PDMS), methyltrimethoxysilane, and trimethylmethoxysilane were purchased from United Chemical Technologies, Inc. (Bristol, Pa., USA). Hexamethyldisilazane (HMDS), poly (methylhydrosiloxane) (PMHS), napthalene, anthracene, phenanthrene, fluorene, fluoranthene, acenaphthylene, 2,3-dimethylphenol, 2,5-dimethylphenol, 2,6-dimethylphenol, 3,4-dimethylphenol, N,N-dimethylaniline, 2-ethylaniline, 2,6-dimethylaniline, 4-ethylaniline, 3-ethylaniline, and n-methylaniline were all purchased from Aldrich Chemical Company, Inc. (Allentown, Pa., USA). 1-decanol, 1-dodecanol, 1-tetradecanol, 1-hexadecanol, 1-octadecanol, and trifluoroacetic acid (TFA) were purchased from Sigma Chemical Company (St. Louis, Mo., USA). Teflon magnetic stirring head (⅜"), methanol (HPLC grade), tetrahydrofuran (THF) (HPLC grade), and disposable borosilicate culture tubes were purchased from Fisher Scientific (Atlanta, Ga., USA). Deionized water (17.8 MΩ), used to prepare all working samples, was obtained from a Barnstead Model 04741 Nanopure deionized water system (Barnstead/Thermodyne, Dubuque, Iowa, USA). Eppendorf polypropylene micro centrifuge tubes (1.5 mL) were purchased from Brinkman Instruments, Inc. (Westbury, N.Y., USA). Upchurch Scientific PEEK tubing of 0.020" i.d.×1/16" o.d. and J&W Scientific 0.4 mm graphite ferrule were purchased from Fisher Scientific (Atlanta, Ga., USA). High temperature 100% silicone adhesive was purchased from Dow Coming Corporation (Midland, Mich., USA).

Figure 1:
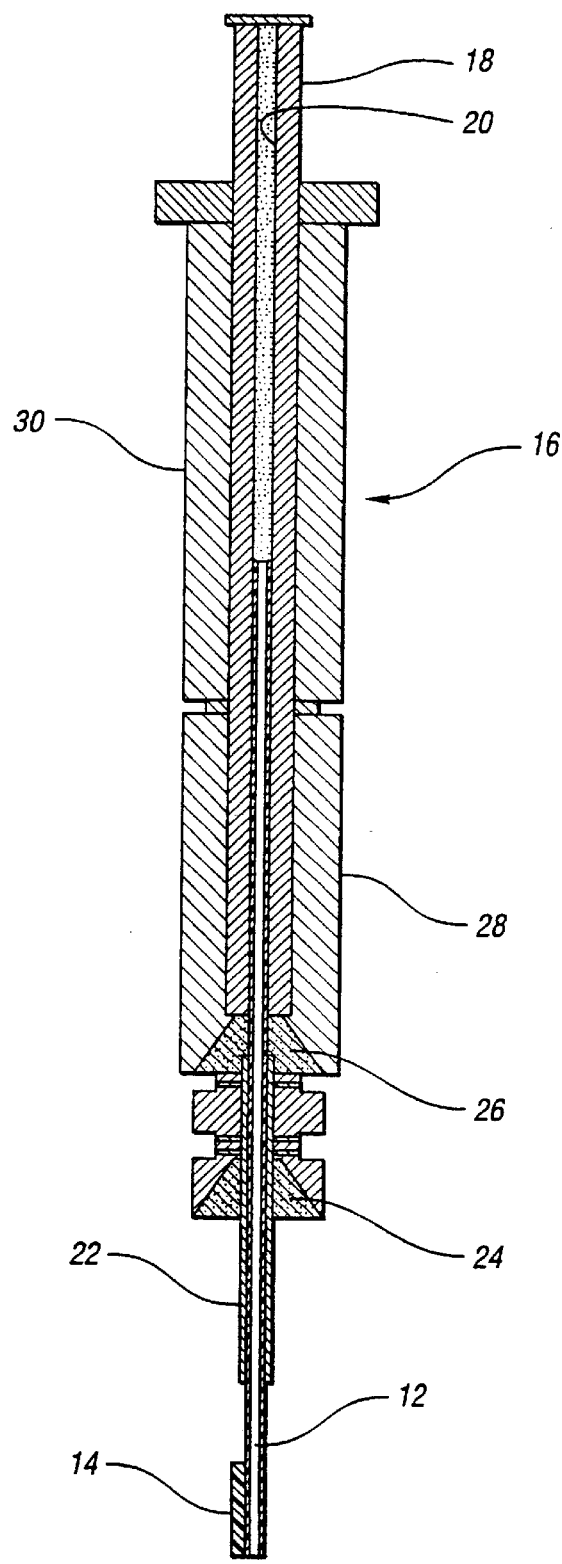
FIG. 1 is a schematic illustration of a syringe which can be used in connection with microextraction fibers made according to the principles of the present invention.

Preparation of SPME syringe 16 (FIG. 1). A 15-cm long fused silica fiber 10 (including ~1 cm at one end with the stationary phase coating 14) was glued into a 15-cm long polyetheretherketone (hereinafter PEEK) tubing 18 using a high-temperature 100% silicone adhesive 20. Approximately 9 cm of the fiber 10 remains glued inside the peek tubing 18. The remainder of the fiber 10 can be moved up and down through the hollow space inside the stainless steel needle 22 (6 cm) of the syringe 16. Close to its distal end, the stainless steel needle 22 is secured in a VALCO™ union 28 using a graphite ferrule 24. On the other side of the union 28, a second graphite ferrule 26 is put on the stainless steel needle end to grip the fused silica fiber 10. This provides an effective seal during the movement of the fiber by the PEEK tubing 18 glued to it. The PEEK tubing 18 runs through the Valco stainless steel fittings 28, 30. Here, the PEEK tubing 18 acts as a plunger. The coated end of the fiber 14 can be moved out of, or retracted back into, the stainless steel needle 22 by moving this plunger in an appropriate direction. During such movements, the cured silicone adhesive 20 in the PEEK tubing 18 prevents the fiber 10 from sliding back through the syringe 16. The ferrule seals 24, 26 prevent either sample or carrier gas from leaking through the syringe 16 during sample desorption inside the injection port.

SPME Fiber Preparation

Preparation of the sol solution. The sol solution was prepared as follows: 300 μL of methyltrimethoxysilane (precursor), 180 mg of hydroxy-terminated PDMS (coating polymer), 30 mg of PMHS (deactivation reagent), and 200 μL of 95% trifluoroacetic acid (TFA, acid catalyst containing 5% water) were thoroughly vortexed for two minutes in a borosilicate culture tube. The mixture was then transferred into an Eppendorf micro centrifuge tube and centrifuged at 13,000 rpm for five minutes. The precipitate at the bottom of the tube, if any, was removed and the top clear sol solution was used for fiber coating.

Sol-gel coating of SPME fiber. The total length of an SPME fiber was 15 cm, including a 1-cm end-segment to be coated by the sol-gel technique. Prior to sol-gel coating, the protective polyimide layer was removed from a 1 cm segment of the fiber at one of its ends. This was accomplished by burning off the polyimide protective layer using a cigarette lighter. The burnt section of the fiber was cleaned with methanol, dried, and then dipped vertically into the sol solution. It was held inside the sol solution for approximately 20 minutes during which a sol-gel coating was formed on the bare outer surface of the fiber end. For each fiber, this coating process was repeated three times, using a freshly prepared sol solution each time. This was followed by the end-capping process. For this, the coated fiber end was dipped into a trimethylmethoxysilane/methanol solution (4:1 v/v). After one minute, the fiber was removed from the end-capping solution and placed in a desiccator at room temperature.

Conditioning of the fiber. The sol-gel PDMS fiber was initially conditioned at 250° C. under helium for approximately one to two hours in the GC injection port. After removal from the injector, the fiber was cooled to room temperature. The fiber was then conditioned again using the same GC conditions for ten minutes. The ten-minute conditioning cycle was repeated a few more times until a stable GC baseline was obtained. The fiber was then ready for SPME and SPME-GC experiments. For thermal stability study, the fiber was conditioned at 250° C., 300° C., 310° C. and 320° C. in the same way.

SPME-GC analysis. After conditioning, the fiber was removed from the GC injection port and cooled down to ambient temperature. The extraction was performed by exposing the coated fiber end to aqueous samples at room temperature. Magnetic stirring was applied to the samples during the extraction process to reduce the equilibration time.[37] After the extraction, the fiber was withdrawn into the needle and removed from the sample matrix. The fiber was then immediately inserted into the heated GC injection port Approximately five minutes were allowed for the analytes to be desorbed from the fiber and get introduced into the GC column for analysis. During desorption, the injection port temperature was maintained at the same level as the fiber conditioning temperature. The thermal desorption step was conducted in the splitless mode, maintaining the column temperature at 40° C. Low column temperature ensured effective solute focusing at the column inlet. On completion of the thermal desorption step, the split vent was opened and kept in that state for the remainder of the chromatographic run. GC separations were conducted using in-house prepared sol-gel coated open tubular PDMS and Ucon columns (10 m×250 μm i.d.).[38] After completion of the sample introduction step, the column temperature was programmed at a rate of 6° C. min$^{-1}$. GC analyses were performed using helium as the carrier gas and FID as the detector. The FID was maintained at 300–350° C. The total run-time was approximately 35 minutes or less.

Preparation of aqueous standard solutions for extraction by SPME. Stock solutions of all PAHs (napthalene, anthracene, phenanthrene, fluorene, fluoranthene, and acenaphthylene) were prepared by dissolving 10 mg of each compound in 10 mL of THF in a 10 mL volumetric flask at room temperature. A 10 μL portion of this standard solution was diluted with deionized water to give an approximately 1 ppm PAHs aqueous solution. For the phenolic compounds (DMP) (2,3-DMP, 2,5-DMP, 2,6-DMP, and 3,4-DMP) the initial stock solutions were prepared in methanol. 500 μL of this stock solution was then diluted with deionized water to give a 50 ppm solution. Standard solutions of aniline derivative (N,N-dimethylaniline, 2-ethylaniline, 2,6-dimethylaniline, 4-ethylaniline, 3-ethylaniline, and N-methylaniline), n-alkanes ($C_{13}$ to $C_{20}$), and aliphatic alcohols (1-decanol, 1-dodecanol, 1-tetradecanol, 1-hexadecanol, and 1-octadecanol) were prepared by dissolving 10 μL of each individual compounds in 10 mL of methanol at room temperature. A 10 μL sample of this standard solution was diluted with deionized water to give aqueous solutions of approximately 1 ppm in concentration.

All vials were silanized prior to use according to the following procedures: the vials were rinsed with 5% solution of HMDS in methylene chloride, followed by placing them in an oven at a temperature of 250° C. for approximately 8 hours. The vials were then sequentially rinsed with methylene chloride, methanol, and deionized water. All other glassware and cross-stir bars were cleaned with Sparkleen detergent and copious amount of deionized water, and then dried in the oven at 100° C. for approximately 1 hour.

Results and Discussions

An important operation in solid-phase microextraction fiber technology is the creation of a stable stationary phase coating at the fiber end. Conventionally, this is done by mere physical deposition of a thick (~100 μm) polymer coating on the outer surface of a solid fused silica fiber at one of its ends. Because of their high thermal stability and enhanced solute diffusion capabilities, polydimethylsiloxanes (PDMS) have gained popularity as SPME coating materials. As has already been mentioned, for most commercial PDMS fibers the thermal stability of such coatings, is less than 270° C. that limits the molecular weight range of analytes that can be handled by SPME-GC technology. Although some research work has already been published regarding the interfacing of SPME with liquid-phase separation techniques (including HPLC and SFC) that can handle larger molecular weight analytes without requiring a high temperature desorption step, such hyphenated techniques are still in their infancy. In those techniques liquid solvents are used to recover the analytes from the fiber for subsequent introduction into the analytical instrument for liquid phase separation. The analyte diffusion in liquids being a slow process, sample recovery/introduction process may be extremely long and often measures in hours. Even in those systems, the limiting factor is the coating stability; not toward high temperature, but toward the solvent used to recover the analytes. "Operational stability," is a term used herein to include both of these coating stability aspects. For obvious reasons, physically coated fibers cannot provide high operational stability in either case.

In this context, a rapid, simple, and reproducible method for the preparation of operationally stable SPME fiber coatings based on sol-gel chemistry was developed. The results obtained show that enhanced operational stability of SPME fibers can be achieved in a simple way using sol-gel technology. In the sol-gel approach, the stationary phase coating was chemically bonded to the surface of the fiber under extraordinarily mild thermal conditions (often at room temperature).

Sol-gel Chemistry of PDMS Coatings in SPME

Table I lists the names and chemical structures of the principal ingredients of the sol-gel coating solution. As can be seen from the table, the sol-gel solution contains appropriate amounts of the coating polymer (hydroxy-terminated polydimethylsiloxane, PDMS), an alkoxysilane precursor (methyltrimethoxysilane, MTMOS), a surface deactivation reagent (polymethylhydrosiloxane, PMHS), and an acid catalyst (TFA containing up to 5% water).

Tetraalkoxysilanes are commonly used as sol-gel precursors. In this example, however, methyltrimethoxysilane (i.e., a methyl derivative of the commonly used precursor—tetramethoxysilane, TMOS) was used. Such a choice aims at overcoming some inherent problems that are faced at the drying step of sol-gel processing, especially for thick films and monoliths.

It is known,[39,40] that a sol-gel material, formed as a result of hydrolysis of the alkoxysilane precursor and subsequent condensation of the hydrolyzed products, may undergo cracking and shrinkage during the drying step. The gel shrinkage and cracking are undesirable effects during the gel-drying process. They originate from the capillary thrust due to solvent evaporation from the gel pores.[41] This problem becomes increasingly significant for sol-gel coatings with thicknesses greater than 0.5–1 $\mu$m.[42-43] In the context of SPME, preservation of the structural integrity is very important for the sol-gel coating to be able to provide desired material properties. As was shown by Mackenzie,[44] the sol-gel network originating from an alkyl-derivative of a tetraalkoxysilane precursor (e.g., methyltrimethoxysilane used in our work), possesses a more open structure and can more effectively relieve stresses during drying, minimizing the cracking tendency. This explains the present use of methyltrimethoxysilane as the sol-gel precursor. Recently, a supercritical drying technique was applied to overcome shrinkage and cracking problems in preparing monolithic columns for capillary electrochromatography.[36]

Two major sets of reactions take place during sol-gel processing[26]: (1) hydrolysis of the precursor and (2) polycondensation of the hydrolyzed products and other sol-gel active moities in the system. These reactions are catalyzed by acids or bases, and lead to the formation of a polymeric network. The hydrolysis reaction of the methyltrimethoxysilane precursor used in this study can be represented by the following equation:[45]

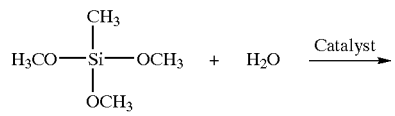

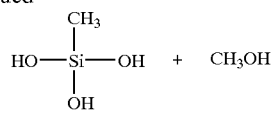

The hydrolyzed products can further undergo polycondensation reactions to produce a three dimensional polymer network. This can be depicted by the following scheme:[43,46]

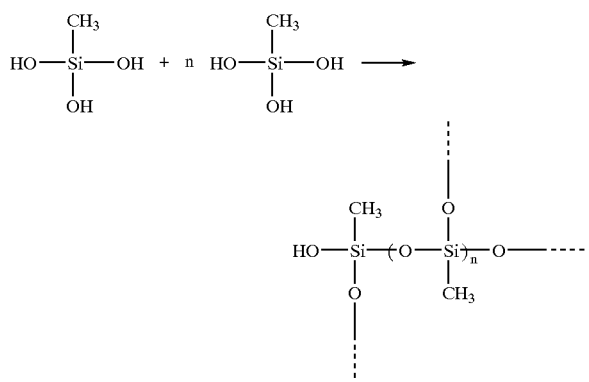

Being hydroxy-terminated, this polymer is sol-gel active.[47-49] Selection of this polymer aimed at chemically binding the PDMS stationary phase to the growing silica network. The chemical reaction involved can be schematically represented by the following equation: In the sol-gel solution we used hydroxy-terminated polydimethylsiloxane as a coating ingredient.

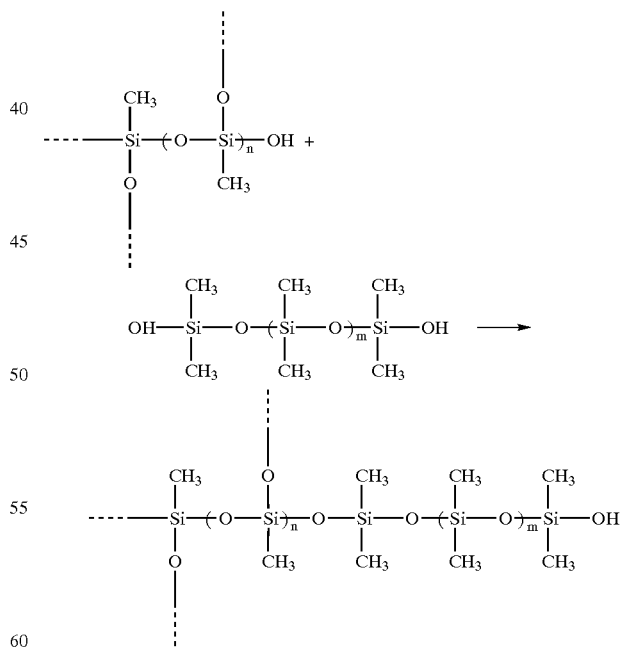

The silanol groups on the fused silica fiber surface can also take part in the condensation reactions and provide chemical anchorage to the polymeric network in the immediate vicinity of the fiber surface. Schematically this reaction can be represented as follows:[50]

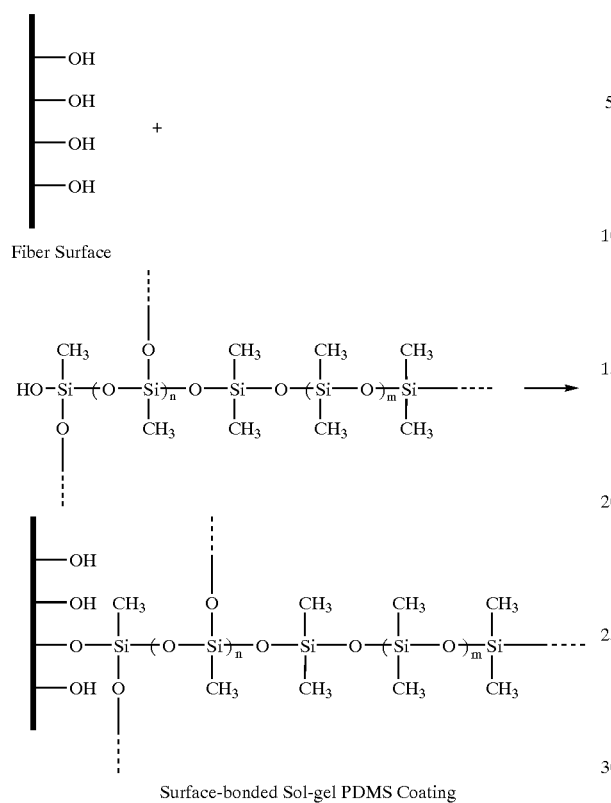

Fiber Surface

Surface-bonded Sol-gel PDMS Coating

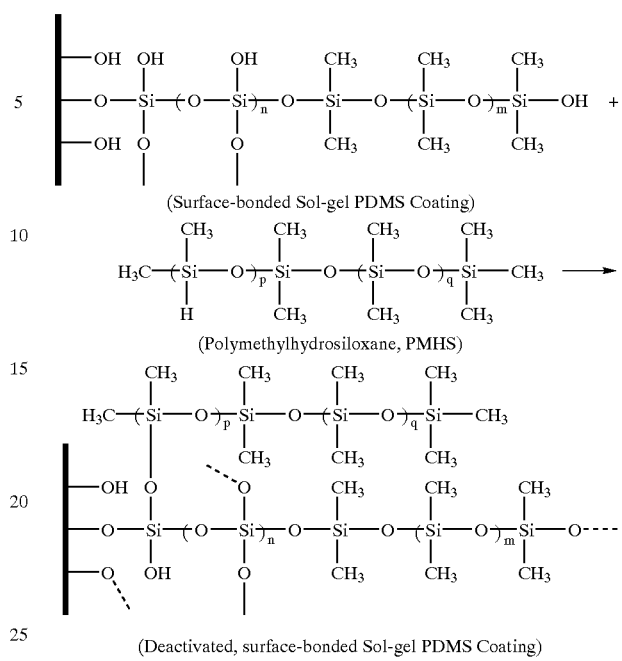

(Surface-bonded Sol-gel PDMS Coating)

(Polymethylhydrosiloxane, PMHS)

(Deactivated, surface-bonded Sol-gel PDMS Coating)

Thus, a surface-bonded polymeric coating is created by dipping the exposed end of the fused silica fiber into the sol solution and allowing it to be there for a certain amount of time. The thickness of this chemically bonded polymeric layer can be controlled by varying the dipping time and the concentrations of the solution ingredients. Higher film thickness can be achieved through repeated dipping operations.

Sol-gel coating technology is characterized by a higher degree of flexibility in the coating composition and selectivity. It should be noted that the surface coating obtained from sol-gel chemistry is not purely organic. It is a composite in nature. The composition of this organic-inorganic coating can be controlled by varying the proportions of the sol solution ingredients. This allows for the possibility of selectivity tuning in SPME fiber technology. By varying the composition of the sol solution, widely diverse surface coatings, ranging from purely inorganic to purely organic can be prepared. Inorganic coatings pose great promise for SPME of volatiles.

Another important ingredient of the used sol solution was polymethylhydrosiloxane (PMHS) which is a well-known surface deactivation reagent in gas chromatography.[51] Molecules of PMHS contain reactive hydrogen atoms capable of derivatizing silanol groups at elevated temperatures. During the coating process, molecules of this ingredient get physically incorporated in the coating. Post-coating thermal conditioning leads to the deactivation of the fiber according to following reaction scheme:

Scheme I. Deactivation of Surface-bonded Sol-gel PDMS Coating with Polymethylhydrosiloxane Since PMHS has very similar chemical structure to that of PDMS, the choice of PMHS as a deactivation reagent appears to be especially appropriate. Its incorporation in the coating structure has little effect on the SPME characteristics of PDMS coatings.

Before conditioning, the coated fibers were treated with a solution of trimethylmethoxysilane to reduce the silanol contents of the coating. Possessing a smaller molecular size than PMHS or hydroxy-terminated PDMS, trimethylmethoxysilane molecules should have greater access to the porous structure of the coating. In parallel with PMHS and hydroxy-terminated PDMS, it provides added deactivation to sol-gel coatings. It should be pointed out that the purpose of deactivation in SPME fiber technology is not identical with that in GC. In GC column technology, deactivation aims at eliminating solute/column surface interactions that are responsible for peak tailings and efficiency losses. In SPME, moderate degrees of polar fiber/solute interactions, can be even advantageous. Such interactions will provide enhanced selectivity for polar compounds in SPME. Addition of appropriate amounts of PMHS and/or trimethylmethoxysilane to the coating solution containing OH-terminated PDMS provides a simple way of maintaining this activity at a desired level. To be able to provide this selectivity advantage, SPME coatings should posses high thermal stability. This is explained by the fact that silanol group-mediated polar interactions between the SPME fiber and the solutes require higher injector temperatures to ensure effective solute desorption. Due to inherent high thermal stability, sol-gel coated PDMS fibers provide efficient release of extracted polar analytes without negative consequences from the use of high temperatures.

Figure 2:
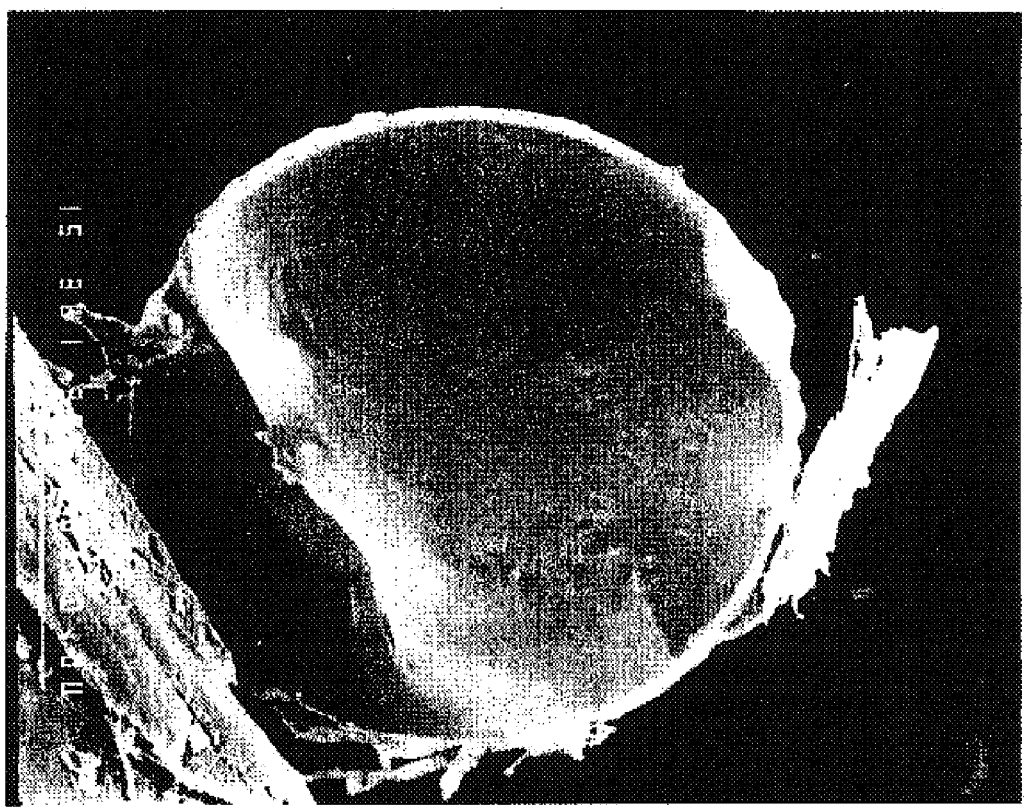
FIG. 2 is a is a cross sectional view of a fiber made according to the present invention, taken with an electron microscope (magnification 360)

The surface characteristics of the sol-gel PDMS fibers were investigated by scanning electron microscopy (SEM) technique. The SEM micrograph provided an estimated film thickness of 10 $\mu$m for the sol-gel PDMS coatings. This is evident from the cross-sectional view of a 200 $\mu$m coated fiber presented in FIG. 2. This thickness is about ten times smaller than the conventional 100-$\mu$m coating thickness used on commercial fused silica fibers. From this perspective, sol-gel coatings might seem disadvantageous for SPME. However, the following discussion will show that this might turn out to be an advantage of the sol-gel coated fibers in solid-phase microextraction.

Figure 3:
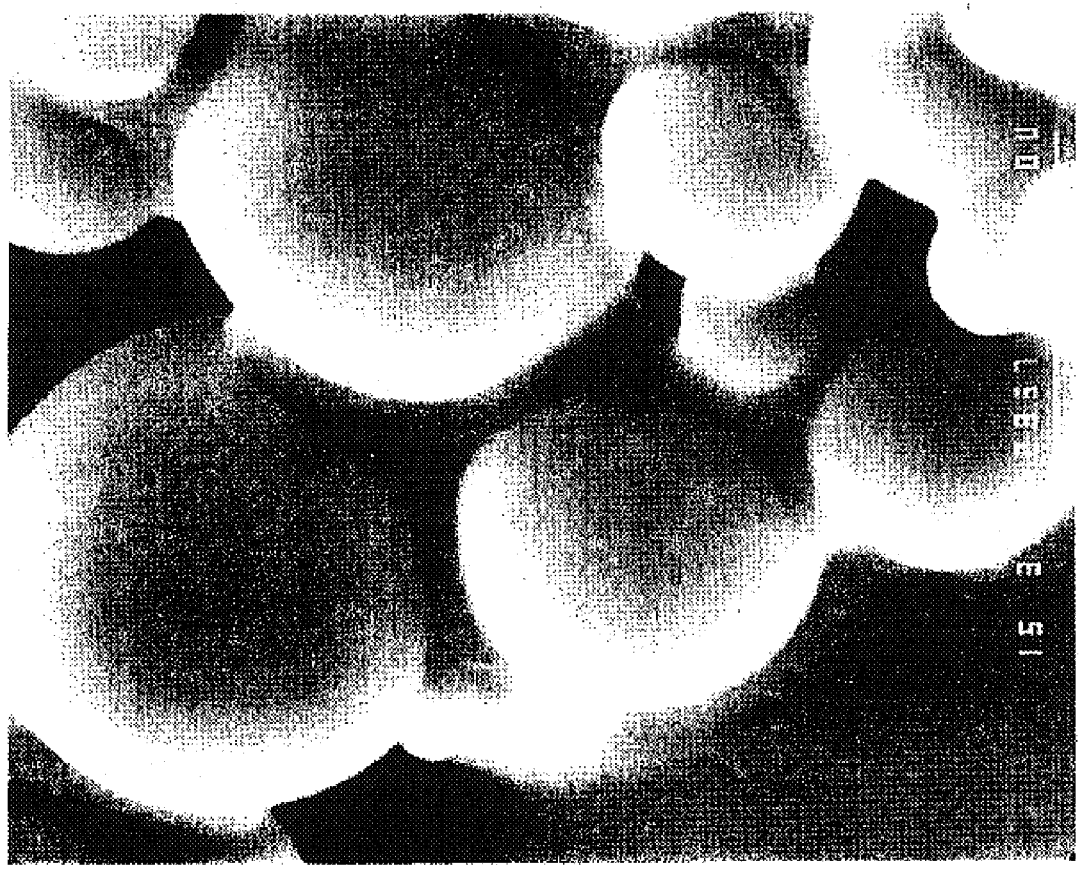
FIG. 3 is an enlarged side view of a portion of sol-gel coating on a fiber made according to the principles of the present invention, taken with an electron microscope (magnification 3,600)

As can be seen from the scanning electron micrograph of the coated surface presented in FIG. 3, the sol-gel coating possesses a porous structure. Such a porous structure was not apparent from the cross-sectional view in FIG. 2 in which the magnification was ten times lower than that of the micrograph presented in FIG. 3. Porous structure of the sol-gel coating should significantly increase the available surface area on the fiber. Consequently, with such a porous coating structure, even an apparently thinner coating will be able to provide enhanced stationary phase loadings, and therefore high fiber sample capacity. The untreated fiber substrate used in this study had a diameter (200 μm) which is twice the diameter of commonly used commercial fibers (100 μm). With the same coating thickness, a larger diameter substrate should provide higher stationary phase loading. Higher surface area of the sol-gel coating should also provide enhanced extraction efficiency in SPME. The smaller coating thickness should help faster mass transfer during extraction as well as analyte desorption processes during sample introduction.

Recently, Lee and coworkers[53] described a porous SPME coating prepared from reversed-phase HPLC packing material mechanically glued to a fiber substrate. Such fibers may not be appropriate for high temperature operations common in SPME-GC, since the glue may undergo decomposition. However, since the used adhesives are highly stable in conventional solvent systems, the glued coatings have the potential to offer stable performance in SPME hyphenated with liquid phase separation techniques. Being chemically bonded to the substrate, sol-gel coated fibers are inherently stable in operations requiring their exposures either to high temperatures or organic solvents. Commercial SPME fibers are not normally recommended to be exposed to organic solvent media.[22]

Figure 4B:
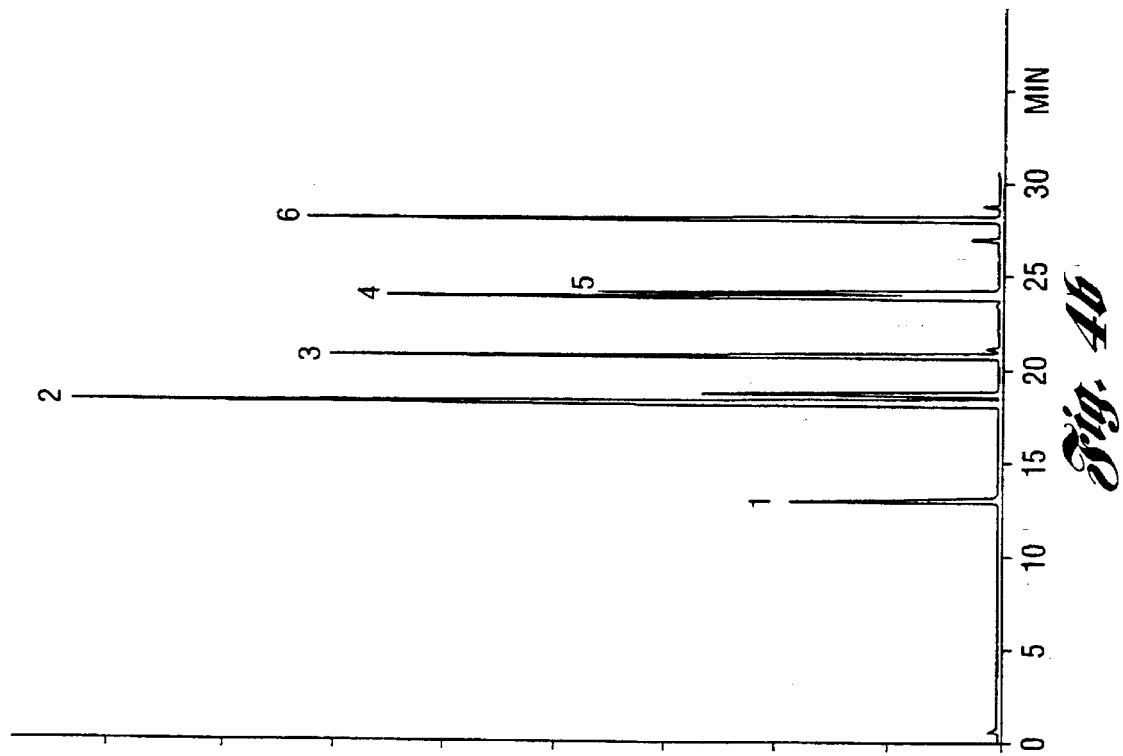
FIGS. 4A and 4B are gas chromatograms of polycyclic aromatic hydrocarbons (PAHs) extracted from solution using fibers made according to the present invention and conditioned at two different temperatures.
Figure 4A:
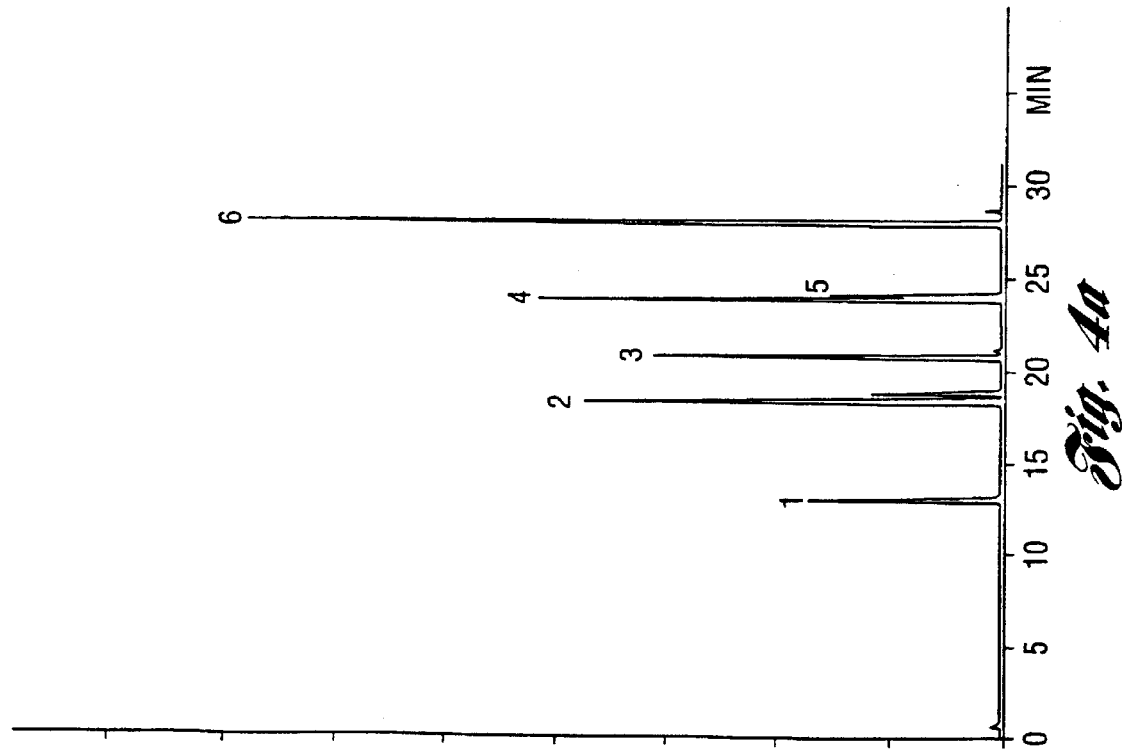

FIGS. 4A and 4B illustrate the thermal stability of sol-gel coated SPME fibers. The gas chromatogram presented in FIG. 4A was obtained from an SPME-GC analysis of polycyclic aromatic hydrocarbons (PAH's) performed after conditioning the fiber at 250° C. for 2–3 hours. In FIG. 4B, the SPME-GC experiments were performed after conditioning the fiber at 320° C. for the same period. The injector temperatures for these two chromatograms were 250° C. and 320° C., respectively. As can be seen from these Figures, the performance of the fiber was not affected at all by high temperature (320° C.) exposure during conditioning and sample introduction. It should be noted that sol-gel coated PDMS fibers did not show any sign of bleeding even at this high injection temperature (320° C.) which is 120° C. higher than the bleeding temperature for conventionally coated PDMS fibers (200° C.) reported by Pawliszyn and coworkers[16]. Chromatogram 4B shows that the use of higher injection temperature also led to some improvement the resolution of the anthracene-phenanthrene pair. This might be due to a more efficient injection and focusing effect resulting from a faster release of the analytes from the fiber at 320° C.

Figure 5:
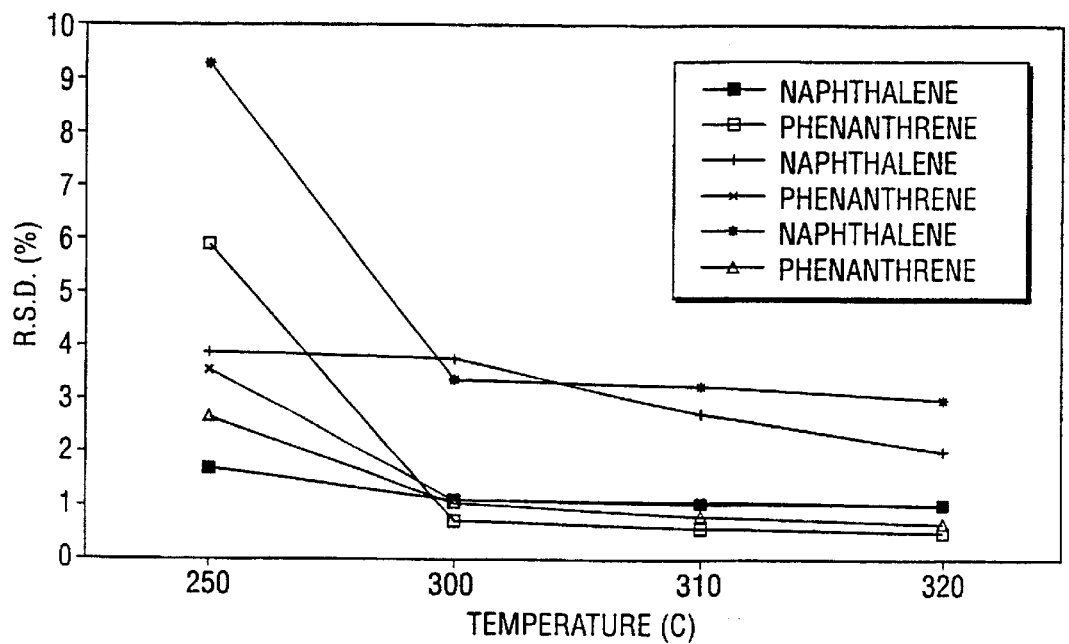
FIG. 5 is a graph showing percent relative standard deviation (RSD) in peak area, n=3, vs conditioning temperature for a fiber prepared according to the present invention using selected PAHs as test solutes.

Experimental data presented in Tables IIA and IIB shows the effects that fiber conditioning and injection temperatures have on the peak area reproducibilities for PAH's. These data suggest that a significant improvement of the peak area reproducibility can be achieved by using higher fiber conditioning and injection temperatures. A continuous decrease in the relative standard deviation (RSD) in the peak areas for the PAH analytes were obtained after conditioning the fiber at increasingly higher temperatures (250° C., 300° C., 310° C., and 320° C.). For example, peak area RSD values obtained for fluoranthene at these four different conditioning temperatures were 2.61%, 1.02%, 0.80%, and 0.64%, respectively. The data for the other PAH components in this nonpolar sample also follow the same trend of repeatability improvement (Table IIA, FIG. 5) with the increase of fiber conditioning and injection temperatures.

Figure 6:
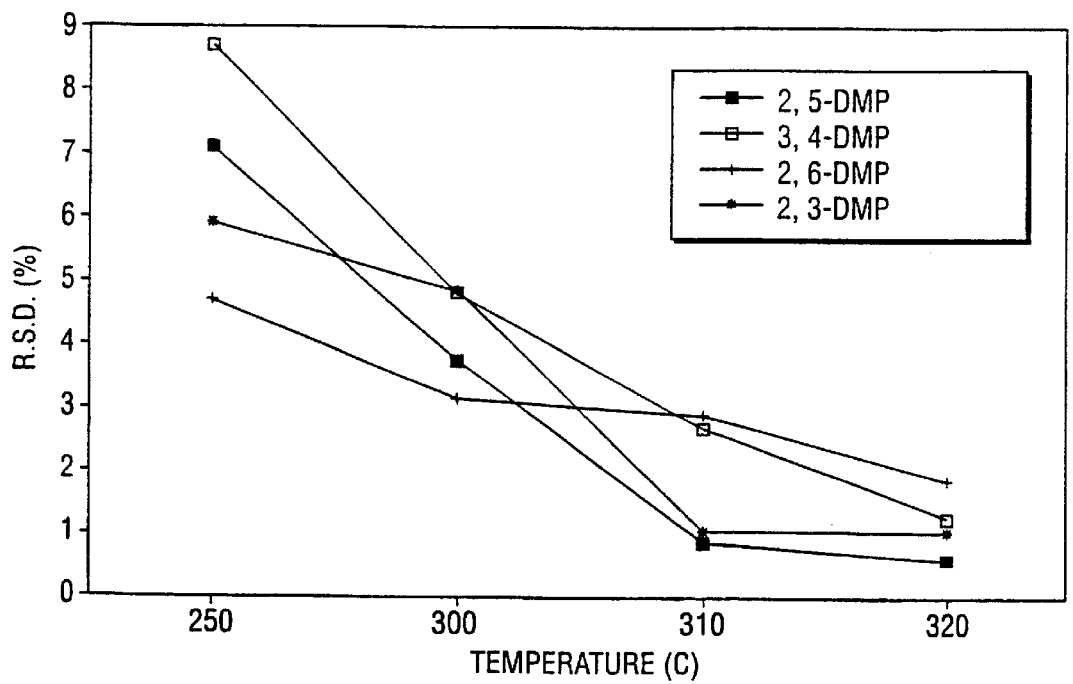
FIG. 6 illustrates peak area percent RSD (n=3) vs conditioning temperature for a fiber prepared according to the present invention using Dimethylphenol (DMP) isomers as test solutes.

An analogous trend was observed for other samples, including polar ones. Table IIIA and FIG. 6 present experimental data for dimethylphenol (DMP) isomers. For example, the peak area RSD value for 2,5-dimethylphenol consistently decreased from 7.14% to 3.74% to 0.84% to 0.58% as the conditioning (and injection) temperature of the fiber was raised from 250° C. to 300° C. to 310° C., and 320° C., respectively. Such a positive effect may be due to more effective release of the extracted analytes at higher injection temperatures and/or due to a better surface deactivation at higher conditioning temperatures.

Figure 9:
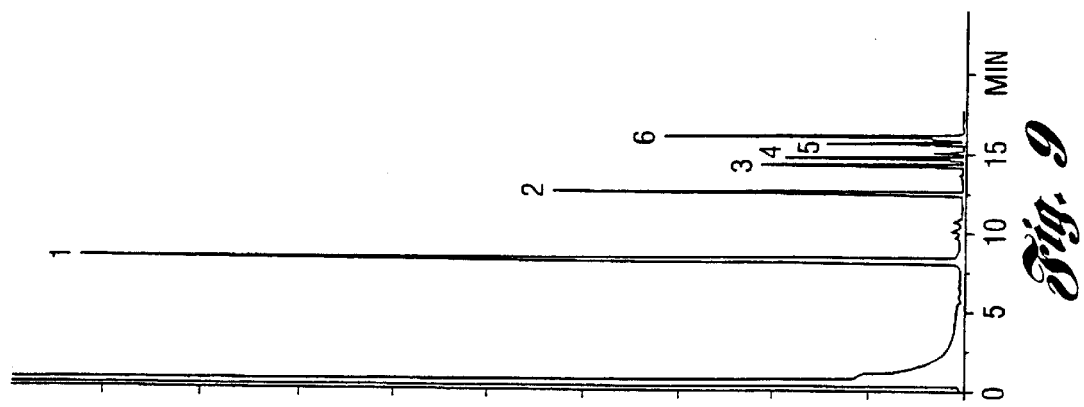
FIGS. 7–9 represent SPME-GC analyses of polar analytes using sol-gel PDMS fibers made according to the present invention.
Figure 8:
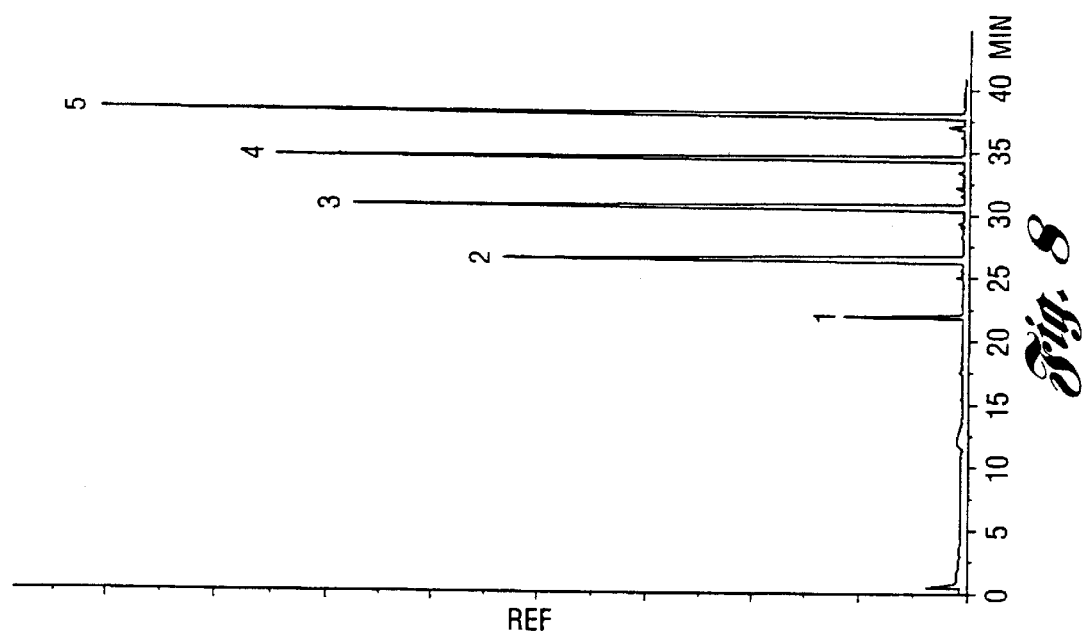
Figure 7:
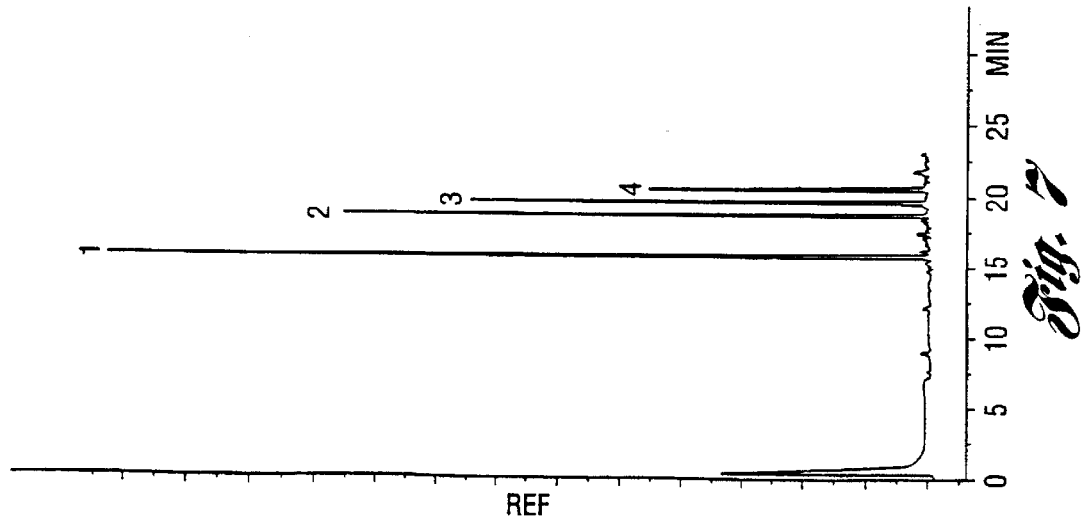
Figure 10:
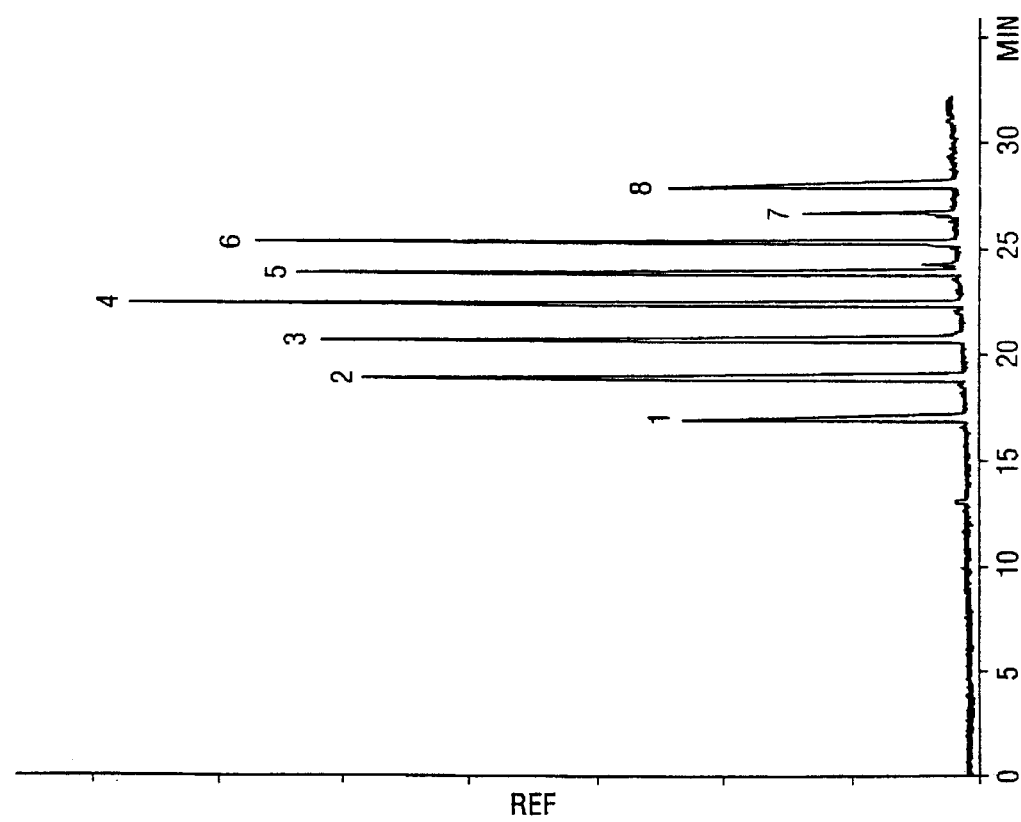
FIG. 10 is a gas chromatographic analysis of nonpolar analytes using sol-gel PDMS microextraction fibers made according to the present invention.
Figure 12:
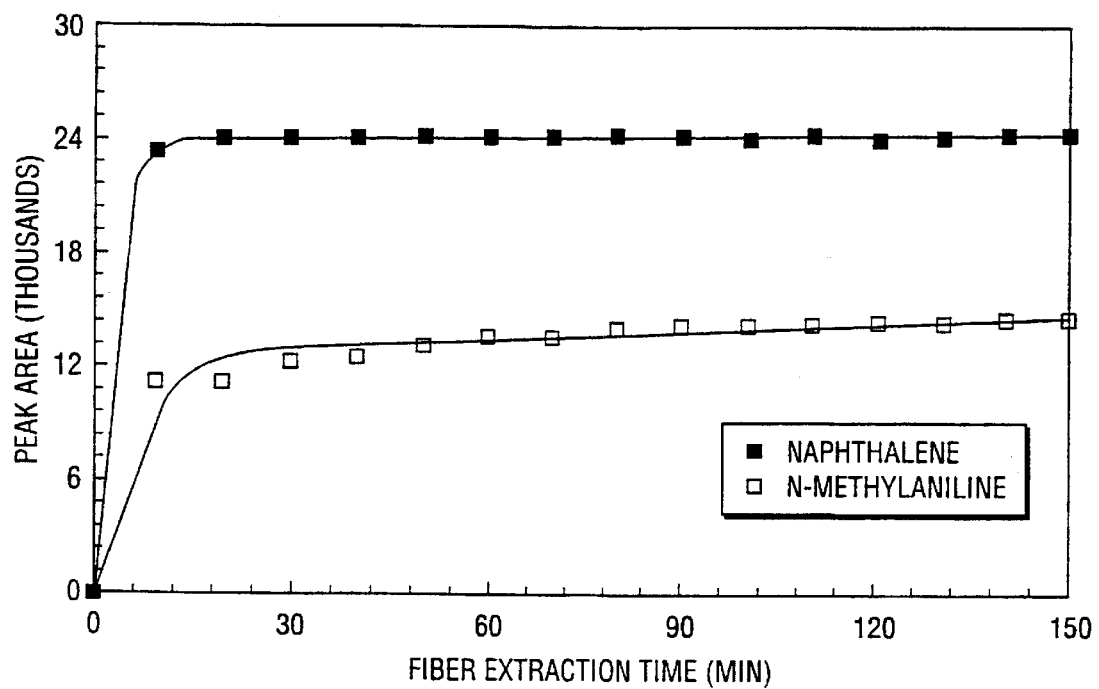
FIG. 12 illustrates fast extraction kinetics on a sol-gel coated PDMS fiber reaching equilibrium within 10 min both for polar and nonpolar analytes.

Sol-gel coated PDMS fibers allowed the extraction of both polar (FIGS. 7–9) and nonpolar (FIGS. 4 and 10) analytes. From SPME perspective, the capability of sol-gel coated PDMS fibers to extract polar compounds is important. As is known, conventionally coated PDMS fibers do not show sufficient selectivity for polar compounds. This difference between PDMS coatings can be explained by comparing the compositional differences between these two types of coatings.

Conventional PDMS coating consists of a thick film of polydimethylsiloxane material which is nonpolar in nature. Naturally, affinity of this nonpolar coating toward polar compounds is low and cannot serve as an effective extraction medium for polar compounds. The situation is significantly different for sol-gel coated PDMS coatings. Individual molecules of hydroxy-terminated PDMS used for sol-gel coating contain terminal silanol groups that are absent in PDMS molecules used for conventional coatings. These hydroxyl groups are meant for chemical bonding of the polymer to the sol-gel network through condensation reaction. Such a chemical bonding requires only one hydroxyl group per molecule. So the second terminal hydroxy group might be free, at least for some of the bonded PDMS molecules. The presence of such a hydroxyl group will make the coating more polar compared with analogous coatings used on conventionally coated PDMS fibers. The sol-gel PDMS coating is an organic-inorganic composite material in which the hydroxy-terminated PDMS molecules are attached to the polar silica network through chemical bonding. Polarity of inorganic and organic components of the composite sol-gel PDMS coating makes it suitable for the efficient extraction of polar compounds.

The SPME-GC results for dimethyl phenol isomers (FIG. 7), aliphatic alcohols (FIG. 8), and aniline derivatives (FIG. 9) are consistent with this hypothesis. Sol-gel chemistry provides an easy tool for fine-tuning this coating polarity through composition adjustments in the sol solution. The high thermal stability of sol-gel coated fibers allowed us to eliminate the sample carryover problem which, as noted by Pawliszyn and coworkers,[16] is inherent in conventionally coated PDMS fibers characterized by low bleed temperatures (200° C.). No carryover problems were observed for the SPME-GC analysis of these polar analytes using sol-gel coated fibers.

Figure 11:
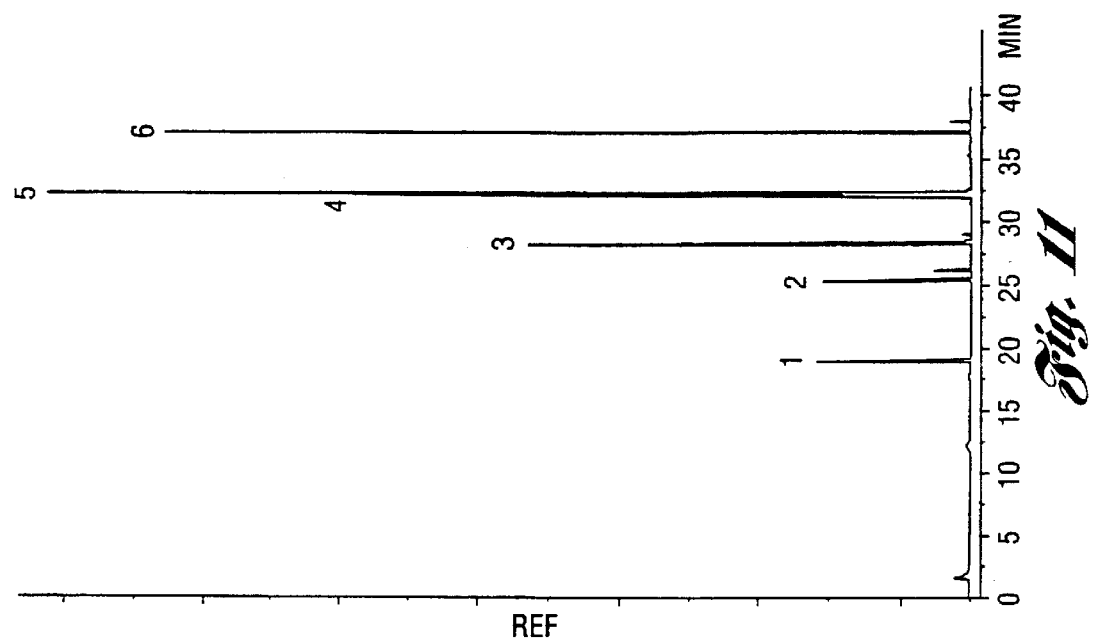
FIG. 11 illustrates high thermal stability of a sol-gel PDMS-coated SPME fiber providing stable performance at a desorption temperature of as high as 360° C.

Experimental results on extraction kinetics for sol-gel coated fibers are presented in FIG. 11 using a polar and a nonpolar analyte. N-methylaniline and naphthalene were chosen to represent these two classes of analytes, respectively. FIG. 11 shows that the extraction equilibrium is reached quite fast. Enhanced surface area of the sol-gel coating is a contributing factor to this. For naphthalene (a nonpolar solute) this equilibrium is practically reached within 10 minutes. Hydrophobic interaction of this nonpolar analyte with the aqueous environment can be expected to serve as the driving force for this fast equilibrium. For N-methylaniline, it takes about an hour for the extraction to reach equilibrium. Attractive forces operating between this polar analyte and water might be responsible for this delay time.

The open tubular GC columns used in this example were also prepared by sol-gel coating technology. Chromatographic performance of such sol-gel columns can be assessed from the quality of separations presented herein and elsewhere.[54] The retention time RSD data presented in Table III (A and B) is also indicative of the high quality of the used sol-gel PDMS column for GC.

Conclusion

Sol-gel chemistry offers a simple and convenient methodology for the creation of advanced material systems with desired structure, composition, and properties. The sol-gel coating technology appears to be universal in nature, and can be applied to prepare chemically bonded coatings on a variety of substrates, including the outer surface of small-diameter cylindrical rods (e.g., SPME fibers) or the inner walls of a small-diameter fused silica capillary (e.g., open tubular separation columns). Both polar and nonpolar surface-bonded coatings can be created using the new technology. Because of chemical bonding between sol-gel PDMS coating and fused silica SPME fibers, sol-gel coated PDMS fibers exhibit higher thermal stability compared with conventionally coated PDMS fibers. The sol-gel PDMS fibers can be routinely used at 320° C. (and higher) without any signs of bleeding, whereas conventionally coated PDMS fibers begin to bleed at 200° C. Enhanced thermal stability of sol-gel coated fibers allows to overcome the sample carryover problem often encountered in SPME of polar solutes with conventional PDMS fibers. Sol-gel coatings possess a porous structure and reduced coating thickness that provide enhanced extraction and mass transfer rates in SPME. High temperature conditioning of sol-gel coated PDMS fibers lead to consistent improvement in peak area repeatability for SPME-GC analysis. Peak area RSD values of <1% can be routinely obtained for PAHs and dimethylphenols on sol-gel PDMS fibers conditioned at 320° C. The presented experimental results clearly demonstrate the potential of sol-gel chemistry in solid-phase microextraction and chromatographic separations.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

ACKNOWLEDGMENT

Financial support for this research was provided, in part, by the University of South Florida Research and Creative Scholarship Grant Program under Grant# 12-13-935-RO. The authors extend their acknowledgment to Ms. Betty R. Loraamm of the University of South Florida Biology Department for technical assistance in electron microscopic experiments.

REFERENCE (1) Lopez-Avila, V.; Bauer, K.; Milanes, J.; Beckert W. F. *J. AOAC Int.* 1993, 76, 864–880.
(2) Majors, R. E. *LC*GC. Int.* 1997, 10, 93–101
(3) Richter, B. E.; Jones, B. A.; Ezzel, J. L.; Porter N. L.; Abdalovic N.; Pohl, C. *Anal. Chem.* 1996, 1033–1039.
(4) Zlotorzynski, A. *Crit. Rev. Anal. Chem.* 1995, 25, 43–76.
(5) Coulibaly, K; Jeon I. J. *Food Rev. Int.* 1996, 12, 131–151.
(6) Hawthorne, S. B.; *Anal. Chem.* 1990, 62, 633A–642A.
(7) Westwood, S. A. (Ed.), *Supercritical Fluid Extraction and Its Use in Chromatographic Sample Preparation*, CRC Press, Boca Raton, Fla., USA, 1993.
(8) Minnich, M. M.; Zimmerman, J. H.; Schumacher, B. A. *J. AOAC Int.* 1996, 1198–1204.
(9) Poole, S. K.; Dean, T. A.; Oudsema J. W., and Poole C. F.; *Anal. Chim. Acta.* 1990, 236, 3–42.
(10) Reighard, T. S.; Olesik S. V.; *Crit. Rev. Anal. Chem.* 1996, 26, 61–99.
(11) van der Vlis, E.; Mazereeuw, M.; Tjaden, U. R.; Irth, H.; van der Greef, J. *J. Chromatogr. A.* 1994,333–341.
(12) Berladi, R. P.; Pawlisyn, J. *Water Pollut. Res. J. Can.* 1989, 24, 179–91.
(13) Arthur, C. L.; Pawliszyn, J. *Anal. Chem.* 1990, 62, 2145.
(14) Zhang, Z.; Yang, M. J.; Pawliszyn, J. *Anal. Chem.* 1994, 66, 844A–53A.
(15) Louch, D.; Motlagh, S.; Pawliszyn J.; *Anal. Chem.* 1992, 64, 1187–1199.
(16) Buchholz, K. D.; Pawliszyn, J. *Anal. Chem.* 1994, 66, 160–167.
(17) Jinno, K.; Muramatsu, T.; Saito, Y.; Kiso, Y.; Magdic, S.; Pawliszyn J. *J. Chromatogr.A.* 1996, 754, 137–144.
(18) Hirata, Y.; Pawliszyn, J. *J. Microcolumn Sep.* 1994, 6, 443–447.
(19) Arthur, C. L.; Potter, D. W.; Buchholz, K. D.; Pawliszyn, J. *LC.GC.* 1992, 10, 656–61.
(20) Arthur, C. L.; Killam, L. M.; Motlagh, S.; Potter, D. W.; Pawliszyn, J. *Environ. Sci. Technol.* 1992, 26, 979–83.
(21) Potter, D. W.; Pawliszyn, J. *J. Chromatogr.* 1992, 625, 247–55.
(22) Supelco Corp., Bellefonte, P A. *Manufacturer data sheet.* 1996.
(23) Blomberg, L. G. *J. Microcol.* 1990, 2, 62–8.
(24) Rotzsche, H. *Stationary Phases in Gas Chromatography*; Elsevier Scientific Publishing Company: Amsterdam, The Netherlands, 1991.
(25) Klein, L. C. *Sol-gel Technology for Thin Films, Fibers, Preforms, Electronics, and Specialty Shapes*; Noyes Publications: Park Ridge, N.J., USA, 1988.
(26) Brinker, C. J.; Scherer G. W.; *Sol-gel Science. The Physics and Chemistry of Sol-gel Processing*, Academic Press, San Diego, USA, 1990.
(27) Livage, J.; Henry, M.; Sanchez, C. *J. Solid St. Chem.* 1988, 18, 259–341.
(28) Fabes, B. D.; Uhlmann, D. R. *J. Am. Ceram. Soc.* 1990, 73(4), 978–88.
(29) Guo, Y; Colon, L. A. *Anal. Chem.* 1995, 67, 2511–16.

(30) Guo, Y.; Colon, L. A.; *Microcolumn Sep.* 1995, 7, 485–491.
(31) Guo, Y.; Imahori, G. A.; Colon, L. A.; *J. Chromatogr. A.* 1996, 744, 17–29.
(32) Guo, Y.; Colon,. L. A. *Chromatographia* 1996, 43, 477–483.
(33) Engelhardt, H.; Cunat-Walter, M. A. *J Chromatogr.* 1995, 716, 27–33.
(34) Wang, D.; Malik, A. *Proc. 18th Intl. Symp. Cap. Chromatogr.*(May 20–24, 1996, Riva del Garda, Italy), P. Sandra & G. Devos (eds.), Huthig Publishers: Germany, 1996, pp. 505–513.
(35) Hayes, J. D.; Malik, A. *J. Chromatogr.* B. 1997, in press.
(36) Hayes, J. D.; Malik, A.*HPCE '97—Final Program* (Jan. 26–30, 1997, Anaheim, Calif., USA), pp. 80–81.
(37) Arthur, C. L.; Killam, L. M.; Buchcholz, K. D.; Pawliszyn, J.; Berg, J. *Anal. Chem.* 1992, 64, 1960–66.
(38) Wang, D.; Chong, S. L.; Malik, A. (manuscript in preparation).
(39) Ramsey J. D. F., "Sol-gel Processing," in *Controlled Particle, Droplet and Bubble Formation*, (D. J. Wedlock ed., Butterworth, U.K., 1994), pp.1–37.
(40) Prakash, S. S.; Brinker C. J.; Hurd A. J.; Rao S. M. *Nature* 1995, 374, 439–443.
(41) Mukherjee S., "Supercritical drying in structural and microstructural evolution of gels: A critical review," in *Ultrastructure Processing of Advanced Ceramics* (Mackenzie J. D. and Ulrich D. R. eds., Wiley, New York, 1988), pp. 747–759.
(42) Scherer, G. W., "Aging and drying of gels," *J. Non-Cryst. Solids* 1988, 100, 77–92
(43) Dislich, H. in *Sol-gel Technology for Thin Films, Fibers,Preforms, Electronics, and Specialty Shapes*, (L. C. Klein ed., Noyes Publications, Park Ridge, N.J., USA, 1988), pp.50–79.
(44) Mackenzie, J. D. in *Hybrid Organic-Inorganic Composites* (ACS Symposium Series 585, American Chemical Society, Washington D.C., 1995), pp.227–236.
(45) Arkles, B.; Steinmetz, J. R.; Zazyczny, J.; and Mehta, P. in *Silicon Compounds: Register and Review*, Huls, 1991, pp.65–73.
(46) Sanchez, C.; Ribot F. *New J. Chem.* 18, 1007–1047 (1994).
(47) Iwamoto, T.; Mackenzie, J. D. *J. Sol-gel Sci. Technol.* 1995, 4, 141–150.
(48) Livage, J. in *Applications of Organometallic Chemistry in the Preparation and Processing of Advanced Materials*, (J. F. Harrod and R. M. Laine Eds., Kluwer Academic Publishing, The Netherlands, 1995), pp.3–25.
(49) Wilkes, G. L.; Orler, B.; Huang, H. H. *Polymer Prep.* 1985, 26, 300.
(50) Stark, F. O., Johnson, O. K.; Vogel, E. G.; Chaffee, R. G.; Lacefield, R. M. *J. Phys. Chem.* 1968, 72, 2750–2754.
(51) Woolley, C. L.; Kong, R. C.; Richter, B. E.; Lee, M. L. *J. High Resolut. Chromatogr./Chromatogr. Commun.* 1984, 7, 329–332.
(52) Chong, S. L.; Wang, D., Malik, A. in progress.
(53) Liu, Y.; Shen, Y.; Lee, M. L. *Anal. Chem.* 1997, 69, 190–95.
(54) Wang D.; Chong S. L.; Malik, A. *Anal. Chem.* Submitted.

TABLE I

Names, functions, and chemical structures of the coating solution ingredients for sol-gel SPME fibers.

| Name of the Ingredient | Function | Chemical Structure |
|---|---|---|
| Methyltrimethoxysilane | Sol-gel precursor | $CH_3O-Si(OCH_3)(OCH_3)-CH_3$ |
| Hydroxy-terminated Poly(dimethylsiloxane) | Coating stationary phase | $HO-Si(CH_3)_2-O-[Si(CH_3)_2-O]_n-Si(CH_3)_2-OH$ |
| Poly(methylhydrosiloxane) | Deactivation reagent | $H_3C-Si(CH_3)(H_3C)-[(O-Si(CH_3)(H))_x-O-(Si(CH_3)-O)_y]_n-Si(CH_3)_2-CH_3$ |
| Trifluoroacetic acid (5% water) | Acid catalyst | $CF_3COOH$ |

TABLE IIA

Peak area repeatability data for polycyclic aromatic hydrocarbons on a sol-gel coated PDMS fiber conditioned at different temperatures. SPME-GC conditions are the same as in FIG. 4.

| | RSD % (n = 3) | | | |
|---|---|---|---|---|
| Compound | 250° C.* | 300° C.* | 310° C.* | 320° C.* |
| Napthalene | 1.67 | 1.04 | 1.01 | 0.98 |
| Acenaphthylene | 3.86 | 3.72 | 2.65 | 2.01 |
| Fluorene | 9.25 | 3.33 | 3.20 | 3.00 |
| Phenanthrene | 5.93 | 0.65 | 0.52 | 0.50 |
| Anthracene | 3.52 | 1.08 | 1.05 | 1.01 |
| Fluoranthene | 2.61 | 1.02 | 0.80 | 0.64 |

*Fiber conditioning temperature

TABLE IIB

Peak area repeatability data for dimethylphenol isomers on a sol-gel coated PDMS fiber conditioned at different temperatures. SPME-GC conditions are the same as in FIG. 7.

| | RSD % (n = 3) | | | |
|---|---|---|---|---|
| Compound | 250° C.* | 300° C.* | 310° C.* | 320° C.* |
| 2,5-dimethylphenol | 7.14 | 3.74 | 0.84 | 0.58 |
| 3,4-dimethylphenol | 4.72 | 3.11 | 2.84 | 1.79 |
| 2,6-dimethylphenol | 5.91 | 4.84 | 1.03 | 1.00 |
| 2,3-dimethylphenol | 8.73 | 4.78 | 2.65 | 1.23 |

*Fiber conditioning temperature

TABLE IIIA

Retention time repeatability data for polycyclic aromatic hydrocarbons in SPME-GC using a sol-gel coated PDMS GC column and a sol-gel coated PDMS fiber conditioned at different temperatures. SPME-GC conditions are the same as in FIG. 4.

| | RSD % (n = 3) | | | |
|---|---|---|---|---|
| Compound | 250° C.* | 300° C.* | 310° C.* | 320° C.* |
| Napthalene | 0.09 | 0.04 | 0.03 | 0.02 |
| Acenaphthylene | 0.03 | 0.03 | 0.02 | 0.02 |
| Fluorene | 0.09 | 0.07 | 0.03 | 0.03 |
| Phenanthrene | 0.09 | 0.11 | 0.07 | 0.02 |
| Anthracene | 0.06 | 0.04 | 0.04 | 0.03 |
| Fluoranthene | 0.04 | 0.02 | 0.02 | 0.02 |

*Fiber conditioning temperature

TABLE IIIB

Retention time repeatability data for dimethylphenol isomers in SPME-GC experiments using a sol-gel coated PDMS GC column and a sol-gel coated PDMS fiber conditioned at different temperatures. SPME-GC conditions are the same as in FIG. 7.

| | RSD % (n = 3) | | | |
|---|---|---|---|---|
| Compound | 250° C.* | 300° C.* | 310° C.* | 320° C.* |
| 2,5-dimethylphenol | 0.04 | 0.03 | 0.03 | 0.02 |
| 3,4-dimethylphenol | 0.09 | 0.07 | 0.03 | 0.03 |
| 2,6-dimethylphenol | 0.04 | 0.02 | 0.03 | 0.02 |
| 2,3-dimethylphenol | 0.07 | 0.04 | 0.04 | 0.03 |

*Fiber conditioning temperature

What is claimed is:

1. A solid phase microextraction fiber comprising
   a. a fiber, and
   b. a deactivated surface-bonded sol-gel coating on a portion of the fiber to form a solid phase microextraction coating on that portion of the fiber:
      said solid-phase microextraction coating being capable of preconcentrating trace organic compounds in various matrices.

2. A solid phase microextraction fiber as set forth in claim 1, wherein said solid phase microextraction coating has the formula:

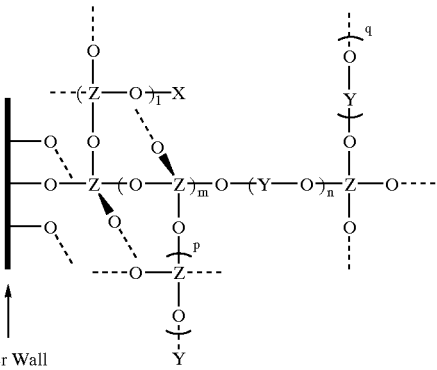

wherein,

X=Residual of a deactivation reagent;

Y=Sol-gel reaction residual of a sol-gel active organic molecule;

Z=Sol-gel precursor-forming element;

l=an integer $\geq 0$;

m=an integer $\geq 0$;

n=an integer $\geq 0$;

p=an integer $\geq 0$;

q=an integer $\geq 0$; and l, m, n, p, and q are not simultaneously zero;

Dotted lines indicate the continuation of the chemical structure with X, Y, Z, or Hydrogen (H) in space.

3. The solid phase microextraction fiber as claimed in claim 2 wherein the residual of the deactivation reagent is a residual of a deactivation reagent selected from the group consisting of polymethylhydrosiloxane and hexamethyldisilazane.

4. The solid phase microextraction fiber as claimed in claim 2 wherein said sol-gel reaction residual is a residual of sol-gel active moieties selected from the group consisting of molecules with hydroxysilane or alkoxysilane functional groups or a combination thereof, polymers, polymethylphenylsiloxane (PMPS), polydimethyldiphenylsiloxane (PDMDPS), polyethyleneglycol (PEG), related polymers, polyethyleneglycol derivatives with sol-gel active functionalities, polyalkylene glycol, macrocyclic molecules, cyclodextrins, crown ethers, calixarenes, alkyl moieties, octadecyl and octyl.

5. The solid phase microextraction fiber as claimed in claim 2 wherein said sol-gel precursor forming element is selected from the group consisting of Si, Al, Ti, and Zr.

6. The solid phase microextraction fiber as set forth in claim 1, wherein said fiber is a solid cylindrical body including an outer surface portion.

7. The solid phase microextraction fiber as set forth in claim 6, wherein said outer surface portion is coated with a sol gel stationary phase.

8. The solid phase microextraction fiber as set forth in claim 1, wherein said fiber is a hollow cylindrical body in the form of a capillary or tube including an inner surface.

9. The solid phase microextraction fiber as set forth in claim 8, wherein said inner surface of said hollow fiber is coated with a sol-gel stationary phase.

10. A method of preparing a solid phase microextraction fibers, comprising the steps of
   a. providing a fiber structure;
   b. providing a sol-gel solution comprising:
      i. a sol-gel precursor,
      ii. an organic material with a least one sol-gel active functional group,
      iii. a sol-gel catalyst,
      iv. a deactivation reagent, and
      v. a solvent system;
   c. reacting at least a portion of the fiber structure with the sol-gel solution under controlled conditions to produce a surface-bonded sol-gel coating on the portion of the fiber structure,
   d. removing the fiber structure from the sol-gel solution; and
   e. heating the coated portion of the fiber structure under controlled conditions to cause the deactivation reagent to react with the surface bonded sol-gel coating
   f. to deactivate and to condition the sol-gel coated portion of the fiber structure.

11. A method as set forth in claim 10, wherein the sol gel precursor includes an alkoxy compound, the organic material comprises monomeric or polymeric material with at least one sol-gel active functional group, the sol gel catalyst being selected from a group consisting of an acid, a base and a fluoride compound, and the deactivation reagent includes a material reactive to hydroxyl groups bonded to the sol-gel precursor forming element or to the fiber surface.

* * * * *